US006251598B1

(12) United States Patent
di Giovine et al.

(10) Patent No.: US 6,251,598 B1
(45) Date of Patent: Jun. 26, 2001

(54) METHODS FOR DIAGNOSING SEPSIS

(75) Inventors: Francesco Saverio di Giovine, Sheffield; Gordon W. Duff, South Yorks, both of (GB)

(73) Assignee: Interleukin Genetics, Inc., Waltham, MA (US)

( * ) Notice: Subject to any disclaimer, the term of this patent is extended or adjusted under 35 U.S.C. 154(b) by 0 days.

(21) Appl. No.: 09/183,850

(22) Filed: Oct. 30, 1998

(51) Int. Cl.[7] .............................. C12Q 1/68; C12P 19/34; C07H 21/04

(52) U.S. Cl. ........................ 435/6; 435/91.2; 536/23.5; 536/24.31; 536/24.33

(58) Field of Search .................. 435/6, 91.2; 536/24.31, 536/24.33, 23.5

(56) References Cited

U.S. PATENT DOCUMENTS

| 4,965,188 | * | 10/1990 | Mullis et al. ............................ 435/6 |
| 5,455,330 | | 10/1995 | Haskill et al. ....................... 530/350 |
| 5,686,246 | * | 11/1997 | Kornman et al. ......................... 435/6 |
| 5,916,891 | | 6/1999 | Adams et al. ........................ 514/256 |

FOREIGN PATENT DOCUMENTS

| 0 677 532 | 10/1995 | (EP) . |
| 0 769 560 | 4/1997 | (EP) . |
| WO 95/01997 | 1/1995 | (WO) . |
| WO 97/25445 | * 7/1997 | (WO) . |
| WO 97/34616 | 9/1997 | (WO) . |
| WO 98/15653 | 4/1998 | (WO) . |
| WO 98/40517 | 9/1998 | (WO) . |
| WO 98/54359 | 12/1998 | (WO) . |
| WO 99/24615 | 5/1999 | (WO) . |

OTHER PUBLICATIONS

Mansfield et al. Gastroenterology. 106:637–642, 1994.*
Fang et al. Anesthesiology. 87: A264, Sep. 1997.*
Clay et al.; "Novel Interleukin–1 Receptor Antagonist Exon Polymorphisms and their use in Allele–Specific mRNA Assessment", Hum. Gen. 97: 723–726 (1996).
Cox et al.; "An Analysis of Linkage Disequilibrium in the Interleukin–1 Gene Cluster, Using a Novel Grouping Method for Multiallelic Markers", Am. J. Hum. Genet. 62: 1180–1188 (1998).
Fang et al.; "Comparison of two Polymorphisms of the Interleukin–1 Gene Family: Interleukin–1 Receptor Antagonist Polymorphisms Contributes to susceptibility to Severe Sepsis", Crit. Care Med. 27(7): 1330–1334 (1999).
Fang et al.; "Genomic Polymorphisms of the Interleukin–1 Gene Family in Patients Suffering from Severe Sepsis", Anesthesiology, 87(3A)Suppl.; pp. A264 (1997).
Fang et al.; "IL–1RA Genomic Polymorphism Associated with Susceptibility to and Outcome of Severe Sepsis", Acta Anaesthesiologia Scandinavica 40 (Suppl. 109): pp. 236(1996).

Kremer, et al., "Interleukin–1,–6 and tumor necrosis factor–alpha release is down–regulated in whole blood from septic patients", Acta Haemmatol. 959(3–4):268–273, (1996).
Lang, et al., "IL–1 receptor antagonist attenuates sepsis–induced alterations in the IGF system and protein synthesis", Am. J. Physiol. 270 (3 Pt 1):E430–437, (1996).
Lang, et al., "Role of central IL–1 in regulating peripheral IGF–I during endotoxemia and sepsis", Am. J. Physiol. 274(4 Pt 2):R956–962, (1998).
Slotman, et al., "Unopposed interleukin–1 is necessary for increased plasma cytokine and eicosanoid levels to develop in severe sepsis", Ann. Surg. 226(1):77–84, (1997).
Kelly, et al., "Is circulating endotoxin the trigger for systemic inflammatory response syndrome seen after injury?", Ann. Surg. 225(5):530–541 (1997).
Seigel, et al., "Physiological and metabolic correlations in human sepsis", Surg. 86:163–193, (1979).
Horn, K.D. "Evolving strategies in the treatment of sepsis and systemic inflammatory response syndrome (SIRS)", QJM 91(4):265–277, (1998).
Sutton, et al., "Endothelial structural integrity is maintained during endotoxic shock in an interleukin–1 type 1 receptor knockout mouse" Shock 7(2):105–110, (1997).
Chang, et al., "Interleukin–1 in Ischemia–Reperfusion Acute Lung Injury", Am. J. Respir. Crit. Care Med. 156(4 Pt 1):1230–1234, (1997).
Pruitt, et al., "Interleukin–1 and interleukin–1 antagonism in sepsis, systematic inflammatory response syndrome, and septic shock" Shock 3:225–251, (1995).
Samson, et al., "Elevated interleukin–1 receptor antagonist levels in pediatric sepsis syndrome" J. Pediatr. 131(4);587–591, (1997).
Atici, et al., "Serum interleukin–1 beta in neonatal sepsis", Acta Pediatr. 85(3):371–374, (1996).
De Bont, et al., "Increased plasma concentrations of interleukin–1 receptor antagonist in neonatal sepsis", Pediatr. Res. 37(5):626–629, (1995).
Blackwell and Christman, "Sepsis and cytokines: current status", Br. J. Anaesth. 77(1):110–117, (1996).
Ling, et al., "Differential effects on interleukin–1 receptor antagonist in cytokine– and endotoxin–treated rats", Am. J. Physiol. 268(2 Pt 1):E255–261, (1995).
Endo, et al., "Plasma levels of interleukin–1 receptor antagonist (IL1ra) and severity of illness in patients with burns", J. Med. 27(1–2):57–71, (1996).
Vallette, et al., "Effect of an interleukin–1 receptor antagonist on the hemodynamic manifestations of group B streptococcal sepsis", Pediatr. Res. 38(5);704–708, (1995).
Meduri, et al., "Persistant elevation of inflammatory cytokines predicts a poor outcome over time", Chest 107(4):1062–1073, (1995).

(List continued on next page.)

Primary Examiner—Carla J. Myers
(74) Attorney, Agent, or Firm—Beth E. Arnold, Esq.; John Quisel; Foley, Hoag & Eliott LLP

(57) ABSTRACT

Methods and kits for detecting polymorphism that are predictive of a subject's susceptibility to developing sepsis are described.

7 Claims, No Drawings

OTHER PUBLICATIONS

Wakefield, et al., "Proinflammatory mediator activity, endogenous antagonists and the systemic inflammatory response intra-abdominal sepsis", *Br. J. Surg.* 85(6):818–825, (1998).

Thijs and Hack, "Time course of cytokine levels in sepsis", *Intensive Care Med.* 21(Suppl. 2):S258–263, (1995).

Goldie, et al., "Natural cytokine antagonists and endogenous antiendotoxin core antibodies in sepsis syndrome", *JAMA* 274(2):172–177, (1995).

Clay, et al., "Novel interleukin–1 receptor antagonist exon polymorphisms and their use in allele–specific mRNA assessment", *Hum. Genet.* 97:723–726, (1996).

Kuster, et al., "Interleukin–1 receptor antagonist and interleukin–6 for early diagnosis of neonatal sepsis 2 days before clinical manifestation", *The Lancet* 352:1271–1277, (1988).

* cited by examiner

METHODS FOR DIAGNOSING SEPSIS

BACKGROUND OF THE INVENTION

Clinical infection is the biological end result of a number of factors, including the nature of the invading organism its intrinsic virulence, the microenvironment of the invaded tissue or organ, and the responsiveness of the host. Any means by which bacteria can be introduced into the tissues can result in an infection. However, the nature of the introduction can influence the severity of the infection and can alter the host's ability to respond. As injuries, a cutaneous laceration, for example, differs from an extensive surgical dissection, which in turn differs from a perforated gastrointestinal viscus. Similarly, a lung infection (a pneumonia) occurring in an area of atelectasis is different from a lung infection that takes place as a result of an aspiration event. Mere presence of pathogens in intact or injured areas does not comprise an infection. A certain critical mass of organisms is necessary in order to sufficiently overcome the host defenses and cause an invasive infection. This level of bacteria is usually stated to be $10^5$ organisms per gram of treatment. A variety of factors can influence the balance between microbial invader and host defenses sufficiently that infections develop at lower levels of bacterial exposure. Necrotic tissue or foreign bodies in a wound are termed adjuvant factors, understood to make infections likely to develop at lower concentrations. Local physiological factors such as impaired circulation also increase local susceptibility to infection. Systemic ailments like diabetes, uremia and AIDS are known to lower the host's resistance to infection, again making it easier for microbes to establish an infection in the tissues.

The severity of an infection in part relates to the extent of the injury that accompanies or precedes it. More severe injury (e.g., an extensive accidental or surgical trauma) interferes with host integrity more substantially, permitting freer access to host tissues and compromising intrinsic host defenses. The severity of an infection depends upon the number and kind of micro-organisms responsible for the infection. If a polymicrobial infection is diagnosed or suspected, early and aggressive antibiotic intervention is commonly warranted, often with broad-spectrum agents with activity against a number of possible invaders.

Certain virulence factors have been associated with specific microorganisms, making invasion carried out by these cells more destructive. Virulence factors are of three general types: 1) biological products produced and secreted by the infecting agent that attack cells in the host or that affect host homeostatic mechanisms to produce clinical disease; 2) structural components of the normal bacterial cell which, when shed within the host's internal environment or when released following death and lysis of the bacterial cell, have toxic effects on the host; 3) responses of the microorganism to antibiotics that make them resistant to these chemotherapeutic agents. Particular microorganisms characteristically manifest specific virulence factors. For example, *Staphylococcus aureus* produces coagulase, which acts as a powerful virulence factor. Staph. and Streptococcus species also produce leukocidins. As a further example, strains of *B. fragilis* produce superoxide dismutase, which converts superoxide anions to hydrogen peroxide; strains of *E. coli* produce catalase, which reduces hydrogen peroxide to water, thereby rendering possible a synergism between these two organisms. A wide variety of other virulence factors have been identified.

The most important structural virulence factor is bacterial endotoxin. Endotoxin is derived from the lipopolysaccharide outer membrane that is found in virtually all Gram negative bacteria. Endotoxin induces an extensive array of biological effects. It is understood directly to stimulate the complement cascade, to provoke platelet aggregation, to induce fever, to activate phagocytosis and the immune system, and to stimulate the synthesis of numerous cytokines. Kremer, et al., "Interleukin-1, -6 and tumor necrosis factor-alpha release is down-regulated in whole blood from septic patients", *Acta Haemmatol.* 95(3–4):268–273, 1996.

Factors relevant to host susceptibility include the ease of entry by which a microorganism first gains access to the host, the impediments placed in the microorganism's path as it spreads within the host, and the ability of the host ultimately to contain the invasion before suffering substantial injury. Certain hosts are known to be more vulnerable than others. Newborns, for example, are particularly prone to severe infections and sepsis. Similarly, pediatric patients can develop sepsis in response to bacterial infections that are much more benign in the adult population. Infections in the elderly are also more likely to progress to sepsis than similar infections in younger patients. Certain pathological conditions are also understood to increase the host's susceptibility to infections and sepsis. Severe trauma, such as that which characterizes major burns, predisposes the patient to microbial infections and sepsis to such an extent that these patients are considered immunocompromised hosts.

It would be desirable to identify those members of vulnerable populations at even more risk for overwhelming infection and its systemic consequences. For example, the newborn with a high temperature must be evaluated for foci of severe infection. This evaluation can include invasive measures such as lumbar puncture in order to rule out meningitis. Often the febrile newborn requires hospitalization and treatment with broad spectrum antibiotics until a source of the fever has been determined. If a subgroup of the newborn population could be identified as having greater risk or less risk of overwhelming infection, diagnostic and therapeutic measures could be tailored to the degree of risk. Lumbar puncture could be restricted to the high-risk infant, for example. Brik, et al., "Evaluation of febrile infants under 3 months of age: is routine lumbar puncture warranted?" *Isr. J Med. Sci.* 33(2):93–97, 1997. Or, for example, low risk infants could be managed as outpatients or discharged quickly from the hospital, offering an important cost-saving in this era of managed care. Durongpisitkul, et al., "The appropriateness of early discharge of hospitalized children with suspected sepsis", *J. Fam. Pract.* 44(1):91–96, 1997. Infants or children at particular risk for certain severe systemic infections could be treated with infection-specific agents, or could be treated earlier or more aggressively.

Host defenses represent an important variable in determining the severity of a clinical infection. Non-specific host defenses serve to limit the initial extent of microbial invasion. Examples include the epiglottis mechanism of the trachea, the vibrissae of the nasal airway, the alveolar macrophage system and the acid environment of the stomach. More specific responses are set into motion on the cellular level once tissue injury or microbial contamination take place. As part of this specific response, the phagocytic-inflammatory components of host defense are initially mobilized with trauma or with the invasion of infecting agents. Phagocytosis and inflammation are intended to contain and destroy the organisms before they gain sufficient systemic access to cause a clinically significant infection. When a small scale infection is localized by these mechanisms, the clinical phenomena of cellulitis or abscess formation result. With more extensive microbial contamination, effective local containment may not be possible. Nonetheless, such containment is the goal of the phagocytic-inflammatory system of host defense.

A multitude of cellular functions contribute to the phase of specific host defense. First and foremost, in response to microbial invasion the host sets in motion the components of inflammation. Only when the stimulus of invading microorganisms becomes sufficiently pronounced do these inflammatory responses rise to the level of clinical infection. Clinical infection then becomes recognizable through the constellation of inflammatory responses that are responsive to the presence of the microorganisms. Rather than a specific response to a particular invader, clinical infection represents a set of nonspecific inflammatory responses elicited by every injury and every microbial contamination. In the ongoing presence of bacteria, the insult is active and progressive, providing a sustained injury that drives the inflammatory response until the offending agents are eradicated.

An early component of this inflammatory response is the complement cascade. This system is understood to be activated by various mechanisms of local tissue injury or microvascular trauma and disruption, leading to the release of opsonins and chemotactic signals that are complement cleavage products having the effect of attracting phagocytes and facilitating their functioning. Mast cells release inflammatory proteins such as kinins and histamines that increase vascular permeability and thus facilitate the access of intravascular proteins and cells into the affected area. Neutrophils are the first phagocytic cells to arrive on the scene. About 24 hours afterwards, activated macrophages arrive.

Macrophages are derived from monocytes that enter the tissues from the bloodstream. Monocytes recruited into the tissues differentiate into macrophages and become activated. In the activated state, macrophages produce a large number of inflammatory and cytokine proteins. An important cytokine released by the activated macrophage is TNF, which has autocrine and paracrine effects. TNF provides autostimulation to monocytes and macrophages to maintain full activation. TNF further stimulates neutrophils to full activation. In acute inflammation such as that found with acute infection, the activated neutrophil acts as the primary phagocyte, responsible for ingesting and killing the invading organisms. These cells may further release free oxygen radicals and lysosomal enzymes into the tissue fluid, causing extracellular killing of pathogens. Side-effects of the release of these cellular cytotoxic products include tissue necrosis, further inflammation and the activation of the coagulation cascade. Furthermore, neutrophils themselves are killed as these processes progress. The end result of this localized response to microbial invasion, with liquified necrotic cells and necrotic tissue, is known clinically as pus.

At the perimeter of the wound, surrounding the central core of necrotic material and cellular debris, additional biological processes are taking place intended to wall off or restrict the penetration of viable microorganisms into unaffected tissues. More neutrophils are attracted from adjacent microvessels by the release of complement cleavage products and TNF. Platelets and coagulation proteins are also activated in the adjacent microcirculation, leading to localized thrombosis. Platelets activated during the process of thrombosis produce thromboxane A2 by way of the cyclooxygenase-thromboxane synthetase pathway of prostaglandin biosynthesis. Thromboxane A2 is a potent vasoconstrictor. The combination of obstruction and vasoconstriction diminishes the inflow of circulation into the localized area of infection, but also blocks the access of pathogens to the general circulation. Activated neutrophils attracted to the periphery of the wound marginate within the microvasculature, leading to endothelial damage, increased vascular permeability and subsequent exudation of cells and serum proteins into the tissue space.

These serum components that leak into the tissues from the microvessels serve the additional function of bringing the building-blocks of wound healing into the infected area, first fibrin, albumin and globulin, and later fibroblasts. Circulating fibroblasts are attracted into the tissues by the growth factors secreted by the activated macrophages within the infected area. Fibroblasts, in turn, produce collagen, a protein that is the basis of scar tissue. If an infection becomes chronic, with the host unable completely to eliminate the pathogen, the infected area ultimately becomes surrounded by a wall of scar tissue formed by the processes of wound healing. In the context of acute or chronic infection, wound healing mechanisms help prevent the escape of the pathogen from the local area into the more general system.

Macrophages provide the connection between the local containment aspect of host defense and the systemic response. Activated macrophages release numerous secretion products, including cytokines that have systemic as well as local effects. Nathan, "Secretory products of macrophages," *J Clin. Invest.* 79:319–326, 1987. The severity of the local inflammatory process may be extreme, due to magnitude of microbial inoculation or microbial virulence, so that the normal autocrine or paracrine mediators of inflammation come to have systemic effect. Systemic dissemination of pathogens or mediators of inflammation result in the host response termed sepsis.

Interleukin-1 (IL-1) is a cytokine released by the macrophage that can be disseminated systemically and induce a systemic response to local injury or infection. IL-1, when locally released, diffuses into the circulation, where it is ultimately carried to the hypothalamus. There, it acts to stimulate the production of prostaglandin-E which acts as an inflammatory mediator and an endogenous pyrogen. IL-1 is known to incite a variety of other systemic responses: it mobilizes neutrophils, stimulates liver production of acute phase proteins and complements, and interacts with tumor necrosis factor (TNF) to amplify the effects of TNF. Dinarello, "Interleukin-1," *Rev. Infect. Disease* 6:51–94, 1984. IL-1 further interacts with other cytokines and growth factors, for example mediating the sepsis induced changes in IGF and the accompanying changes in muscle protein synthesis. Lang, et al, "IL-1 receptor antagonist attenuates sepsis-induced alterations in the IGF system and protein synthesis", *Am. J Physiol.* 270(3 Pt 1):E430–437, 1996; Lang, et al, "Role of central IL-1 in regulating peripheral IGF-I during endotoxemia and sepsis", *Am. J PhysioL* 272(4 Pt 2):R956–962, 1998. IL-1 is also responsible for the increases in circulating eicosanoid levels, levels of IL-6 and levels of TNF. Slotman, et al, "Interleukin-1 mediates increased plasma levels of eicosanoids and cytokines in patients with sepsis syndrome", *Shock* 4(5):318–323, 1995; Slotman, et al, "Unopposed interleukin-1 is necessary for increased plasma cytokine and eicosanoid levels to develop in severe sepsis", *Ann. Surg.* 226(1):77–84, 1997.

When the systemic effects of host defense response accompany a microbial invasion, the condition is termed "sepsis." Standard definitions do not exist for such terms as sepsis, septicemia, septic syndrome and septic response. Most connotations of these terms associate them with severe systemic infection. Traditionally, the most common offending agents were thought to be gram negative bacteria; more recently it has been observed that patients can have characteristic responses of sepsis without a clearly identifiable inciting microbe. The term sepsis has thus come to be associated with any systemic response to overwhelming infection or other severe insult. Kelly, et al, "Is circulating endotoxin the trigger for the systemic inflammatory response syndrome seen after injury?" *Ann. Surg.* 225(5): 530–541; discussion 542–543, 1997.

The term "systemic inflammatory response syndrome" (SIRS) has been applied to a set of responses consistent with what is commonly understood to be sepsis. American College of Chest Physicians/Society of Critical Care Medicine Consensus Conference, "Definition for sepsis and organ failure and guidelines for the use of innovative therapies in sepsis," *Crit. Care Med.* 20:864, 1992. The elements of this syndrome revolve around certain clinical findings, including temperature, heart rate, respiratory rate or PaCO2 and white cell count. SIRS criteria have been applied in prospective studies considering the prognosis of patients with septic-related diagnoses.

The SIRS criteria are thought by some authors to be too broad to have clinical value. One study followed 1101 patients admitted to intensive care units, finding about half of the admissions to have manifestations of SIRS, with 16% to have findings consistent with established sepsis, 5% to have findings consistent with severe sepsis and 6% to be in the state of septic shock. Salvo, et al., "The Italian SEPSIS study: preliminary results on the incidence and evolution of SIRS, sepsis, severe sepsis, and septic shock", *Intensive Care Med.* 21(Supple 2):S244–249, 1995. The mortality rates rise with the severity of the septic elements: about one-fourth of those patients with SIRS died, 36% with sepsis, 52% with severe sepsis, and 81% with septic shock. Late mortality after sepsis and septic shock is equally poor, with only 30% surviving the first year after hospital admission. Schoenberg, et al. "Outcome of patients with sepsis and shock after ICU treatment", *Langenbecks Arch. Surg.* 383(1):44–48, 1998.

The Salvo study introduced a set of gradations in inflammatory severity that parallels the staging system proposed by Siegel et al. in the earlier surgical literature. Siegel et al., "physiologic and metabolic correlations in human sepsis," *Surg.* 86:163–193, 1979. According to Siegel's system, the extent of the septic response is assessed according to four criteria: hyperdynamic cardiac parameters, reduced peripheral vascular resistance, narrowed arteriovenous oxygen difference, and abnormal serum lactic acid levels. Within this staging system, Stage A is characterized by a physiologic stress response, Stage B represents an exaggerated stress response, Stage C is the onset of septic shock and Stage D is low output failure and established shock. Individual patients do not necessarily progress sequentially from one stage to another. A patient can decompensate from Stage A to Stage C with no Stage B interval. Alternatively, with modem technology, a patient can be sustained in Stage B for a prolonged time, setting the stage for a number of sepsis-related sequelae such as multiple organ failure even though no frank shock has supervened. It would be desirable to identify those patients whose septic course is more likely to be progressive. This would allow early and aggressive therapies to be directed towards those patients who face the most dire prognoses. Horn, K. D. "Evolving strategies in the treatment of sepsis and systemic inflammatory response syndrome (SIRS)", *QJM* 91(4):265–277, 1998. Similarly if a patient is likely to remain in a prolonged Stage B, supportive measures can be instituted at early stages to forestall the consequences of multiple organ failure.

Alternate hypotheses have been proposed to explain the progression of sepsis and the occurrence of sepsis-related sequelae that can be as lethal as Stage D septic shock. One hypothesis suggests that the primary defect in sepsis is mitochondrial injury, whereby the mitochondria are unable to metabolize oxygen and related substrates. Mela et al., "Defective oxidative metabolism of rat liver mitochondria in hemorrhagic and endotoxin shock," *Am. J. Physiol.* 220:571–580, 1971. A second hypothesis focuses on the parallels between the systemic septic response and the local response to tissue infection and injury. This hypothesis is supported by an extensive body of experimental and clinical literature. According to this view, systemic complement activation and systemic macrophage activation lead to systemic neutrophil activation, in analogy to the interrelated local behaviors of complement, macrophages and neutrophils. Schirmer et al., "Complement activation produces hemodynamic changes characteristic of sepsis," *Arch. Surg.* 123:316–321, 1989; Schirmer et al., "Recombinant human TNF produces hemodynamic changes characteristic of sepsis and endotoxemia," *Arch. Surg.* 124:445–448, 1989.

When neutrophils are systemically activated, their actions are diffuse and unchanneled. Systemic neutrophil activation also entails diffuse neutrophil margination. In this situation, the neutrophils attach to the endothelium of vessels throughout the body and exert their effects on all tissues they encounter. Endothelial injury results from secretion of neutrophil products, leading to increased vascular permeability. As neutrophils attach to the endothelium and enter the tissues, they also release oxygen free radicals and lysoymal enzymes which contribute to a systemic inflammatory response. Release of these products into the bloodstream catalyzes further systemic responses. Entry of neutrophils into local tissues previously unaffected by infection allows disseminated tissue damage to take place.

Endothelial injury from the secreted products of activated neutrophils further results in platelet activation and induction of the coagulation cascade. Sutton, et al, "Endothelial structural integrity is maintained during endotoxic shock in an interleukin-1 type 1 receptor knockout mouse" *Shock* 7(2):105–110, 1997 Thromboxane A2 is thereupon released. As a result of these processes, plugs are formed in the microvascular system from the combination of neutrophils, platelets and fibrin. These plugs, combined with the vasoconstrictive effects of thromboxane, cause focal tissue ischemia Chang, et al., "Interleukin-1 in ischemia-reperfusion acute lung injury", *Am. J. Respir. Crit. Care Med.* 156(4 Pt 1):1230–1234, 1997. Focal ischemia in tissues leads to focal necrosis. Hinshaw, L. B. "Sepsis/septic shock: participation of the microcirculation: an abbreviated review", *Crit. Care Med.* 24(6):1072–1078, 1996. A physiological paradox comes to exist, where microcirculatory ischemia exists despite the presence of a hyperdynamic circulation.

Tissue necrosis, both locally and distantly, in its turn provides a stimulus for further inflammation. Rapid evolution of these processes can lead to the progression from Stage C sepsis to Stage D sepsis, with a fatal outcome common. Alternatively, if Stage B sepsis is prolonged in the face of these microcirculatory events, focal but disseminated tissue necrosis can extend to culminate in multiple organ failure.

It is understood that the systemic inflammatory response has beneficial effects as part of the host's immune system. Ertel, et al., "Downregulation of proinflammatory cytokine release in whole blood from septic patients", *Blood* 85(5): 1341–1347, 1995. Cytokine release has been identified following surgical procedures, with more severe operative trauma occasioning more extensive release Pruitt et al., "Interleukin-1 and interleukin-1 antagonist [IL-IRN] in sepsis, systemic inflammatory response syndrome and septic shock," *Shock* 3:235–251, 1995. Conversely, defective response in cytokine production can lead to inadequate immune response to stress or infectious insult. Samson, et al., "Elevated interleukin-1 receptor antagonist levels in pediatric sepsis syndrome" *J. Pediatr.* 131(4):587–591, 1997. Neonates with sepsis, for example, have been found to have lower levels of serum IL-1 and higher levels of IL-1RN vs. normal controls. Atici, et al., "Serum interleukin-1 beta in neonatal sepsis", *Acta Pediatr.* 85(3):371–374, 1996; de Bont, et al., "Increased plasma concentrations of interleukin-1 receptor antagonist in neonatal sepsis", *Pedatr. Res.* 37(5):626–629, 1995.

It is therefore desirable to identify those whose interleukin immune feedback systems make them more vulnerable to overwhelming, initially occult sepsis. However, it is further recognized that an excessively vigorous systemic inflammatory response comprises the patterns of sepsis that culminate in such disastrous events as disseminated intravascular coagulation, multiple organ failure and cardiovascular collapse. Aikawa has termed the excessive production of cytokines that culminates in this generalized autoinflammatory reaction "cytokine storm." Aikawa, N. "Cytokine storm in the pathogenesis of multiple organ dysfunction syndrome associated with surgical insults" *Nippon Geka Gakkai Zasshi* 97(9):771–777, 1996. It would be clinically useful to identify patients at heightened risk for exaggerated inflammatory response who may therefore be prone to its undesirable sequelae.

Current understanding has highlighted the role played in systemic inflammation by various cytokines. Blackwell and Christman, "Sepsis and cytokines: current status", *Br. J. Anaesth.* 77(1):110–117, 1996. Excessive IL-1 production, for example, has been linked to the development of hypotension, shock, adult respiratory distress syndrome (ARDS), multiple organ failure, hematological abnormalities and death in patients and experimental animals with sepsis. Pruitt et al., supra. IL-1 and TNF have been implicated in producing the metabolic alterations found in sepsis and injury. Ling, et al., "Differential effects on interleukin-1 receptor antagonist in cytokine- and endotoxin-treated rats", *Am. J Physiol.* 268(2 Pt 1):E255–261, 1995. Similarly, trauma patients have been found to demonstrate elevated levels of inflammatory mediators, consistent with the clinical features of inflammation in these conditions. Endo, et al. "Plasma levels of interleukin-1 receptor antagonist (IL-1ra) and severity of illness in patients with burns", *J. Med* 27(1–2):57–71, 1996. Cytokines, particularly IL-1 and TNF, are identified as coordinating the cascade of interactions between leukocytes and endothelial cells which result in the types of tissue damage discussed above as characteristic of sepsis. Shanley, et al., "The role of cyotkines and adhesion molecules in the development of inflammatory injury", *Mol. Med. Today* 1(1):40–45, 1995. The presence of thrombin is understood to stimulate further production of IL-1 and TNF, thereby perpetuating the cycles of thrombosis and DIC that can accompany sepsis. Hoffman and Cooper, "Thrombin enhances monocyte secretion of tumor necrosis factor and interleukin-1 beta by two distinct mechanisms", *Blood Cells Mol. Dis.* 21(2):156–167, 1995; Gando, et al., "Cytokines, soluble thrombomodulin and disseminated intravascular coagulation in patients with systemic inflammatory response syndrome" *Thromb. Res.* 80(6):519–526, 1995.

Many current approaches for treating sepsis and its sequelae attempt to modulate cytokine interactions within the inflammatory cascade. Since IL-1 and TNF have been identified as circulating factors that integrate and perpetuate these effects, therapies designed to antagonize the effects of these agents can be designed to have clinical utility in ameliorating the sequences involved in sepsis. For example, IL-1 has been identified as playing an important role in Group B streptococcal sepsis and septic shock in the newborn; it is suggested that IL1-RN treatment may ameliorate the cardiovascular alterations associated with this disease in the newborn population. Vallette, et al., "Effect of an interleukin-1 receptor antagonist on the hemodynamic manifestations of group B streptococcal sepsis", *Pediatr. Res.* 38(5):704–708, 1995. Other data suggest, however, that specific cytokine inhibitors may not be effective in modulating inflammation induced by gram-negative bacterial products. Paris, et al., "Effect of interleukin-1 receptor antagonist and soluble tumor necrosis factor receptor in animal models of infection", *J. Infect. Dis.* 171(1):161–169, 1995. Therefore it would be useful to identify those diseases where cytokine modification is likely to work, and those where it is likely to be ineffective or hazardous.

It would furthermore be clinically advantageous to identify those patients with sepsis in whom early intervention strategies may forestall potentially devastating complications. For example, elevated levels of IL-1 have been identified as markers for poor prognosis in patients with ARDS, a common concomitant of sepsis. Meduri, et al., "Persistent elevation of inflammatory cytokines predicts a poor outcome in ARDS. Plasma IL-1 beta and IL-6 levels are consistent and efficient predictors of outcome over time", *Chest* 107(4):1062–1073, 1995. Determining whether a patient falls into the subgroup destined for a poor outcome can motivate the clinician to undertake early and perhaps more ambitious therapies for the ARDS, for example, early glucacorticoid treatment or early institution of extracorporeal membrane oxygenator. Headley, et al, "Infections and the inflammatory response in acute respiratory distress syndrome", *Chest* 111(5):1306–1321, 1997. Bonten, et al., "The systemic inflammatory response in the development of ventilator-associated pneumonia", *Am. J. Respir. Crit. Care Med.* 156(4 Pt 1): 1105–1113, 1997. Similarly, a patient at high risk for poor outcome may merit early, aggressive, continuous and/or multiple antibiotic treatment. Mercer-Jones, et al., "Continuous antibiotic treatment for experimental abdominal sepsis: effects on organ inflammatory cytokine expression and neutrophil sequestration" *Br. J. Surg.* 85(3):385–389, 1998. Steroids may be indicated to treat the global inflammatory response in those patients who are identified as inflammation overreactors. Jones and Lowes, "The systemic inflammatory response syndrome as a predictor of bacteraemia and outcome from sepsis", *QJM* 89(7):515–522, 1996. Lefering and Neugebauer, "Steroid controversy in sepsis and septic shock: a meta-analysis", *Crit. Care Med.* 23(7):1294–1303, 1995. Plasmapheresis may be appropriate to remove the inflammatory elements from the septic patient's bloodstream in those who are prone to exaggerated inflammatory response. Haupt, et al., "Selective cytoldne release induced by serum and separated plasma from septic patients", *Eur. J Surg.* 162(10):769–776, 1996; Stegmayr, B. G. "Plasmapheresis in severe sepsis or septic shock", *Blood Purif.* 14(1):94–101, 1996. Manipulating the complement system may provide an additional strategy for treating the patient with severe inflammatory response in sepsis. Kirschfink M. "Controlling the complement system in inflammation", *Immunopharmacology* 38(1–2):51–62, 1997. Or, realizing the additional inflammatory burden imposed by surgery in certain septic patients may further provide the clinician information about the timing of surgical interventions in sepsis, and will guide the clinician in possible forms of adjuvant therapy.

Recognizing these potential prognostic and therapeutic implications of cytokine release has led investigators and clinicians to measure cytokine levels and try to correlate them with clinical situations. van der Poll, et al, "Anti-inflammatory cytokine responses during clinical sepsis and experimental endotoxernia: sequential measurements of plasma soluble interleukin (IL)-1 receptor type II, IL-10, and IL-13", J. Infect. Dis. 175(1):118–122, 1997. For example, IL-1ra has been measured in high risk neonates and noted to be elevated one or more days before the onset of clinical sepsis (Kuester, H. et al., (1998) *The Lancet* 352:1271–1277). Unfortunately, under varying clinical circumstances, there has been marked variability in the data. For example, during the development of organ failure and death as a result of intra-abdominal sepsis, levels of proinflammatory mediators and their endogenous antagonists vary considerably. Wakefield, et al., "Proinflammatory mediator activity, endogenous antagonists and the systemic inflammatory response in intra-abdominal sepsis. Scottish Sepsis Intervention Group", *Br. J. Surg.* 85(6):818–825, 1998. Some authors find that IL-1 levels correlate positively with poor prognosis in sepsis, (Thijs and Hack, "Time course of cytokine levels in sepsis", *Intensive Care Med.* 21(Suppl. 2):S258–263, 1995), while others fail to find this correlation. Goldie, et al., "Natural cytokine antagonists and endogenous antiendotoxin core antibodies in sepsis syndrome", *JAMA* 274(2):172–177, 1995.

A means for measuring a patient's propensity for exaggerated inflammatory response as an indicator of his or her response to septic stimuli is needed.

SUMMARY OF THE INVENTION

In one aspect, the invention features assays for determining a subject's susceptibility to developing sepsis or prognosticating on the rapidity and/or ultimate progression of sepsis in that subject. In one embodiment, the method comprises the step of genotyping a nucleic acid sample obtained from the subject to determine at least one allele of an IL-1 proinflammatory haplotype.

For example, an allele of an IL-1 proinflammatory haplotype can be detected by: 1) performing a hybridization reaction between the nucleic acid sample and a probe or probes that are capable of hybridizing to an allele of an IL-1 haplotype in the subject; 2) sequencing at least a portion of at least one allele of an IL-1 haplotype; or 3) determining the electrophoretic mobility of at least one allele of an IL-1 haplotype or a component thereof. In another preferred embodiment, a component of an IL-1 haplotype is subject to an amplification step, prior to performance of the detection step. Preferred amplification steps are selected from the group consisting of: the polymerase chain reaction (PCR), the ligase chain reaction (LCR), strand displacement amplification (SDA), cloning, and variations of the above (e.g. RT-PCR and allele specific amplification). In a particularly preferred embodiment, the sample is hybridized with a set of primers, which hybridize 5' and 3' to a sense or antisense sequence of an allele of an IL-1 haplotype and is subject to a PCR amplification.

In another aspect, the invention features kits for performing the above-described assays. The kit can include DNA sample collection means and a means for determining at least one allele of an IL-1 proinflammatory haplotype of the subject. The kit may also comprise control samples or standards.

Information obtained using the assays and kits described herein (alone or in conjunction with information on another genetic defect or environmental factor, which contributes to sepsis) is useful for predicting whether a subject is likely to develop sepsis. In addition, the information alone or in conjunction with information on another genetic defect contributing to sepsis (the genetic profile of sepsis) allows customization of sepsis therapy to the individual's genetic profile. For example, this information can enable a doctor to: 1) more effectively prescribe a drug that will address the molecular basis of the cascade resulting in sepsis; and 2) better determine the appropriate dosage of a particular sepsis drug for a particular patient.

The ability to target patient populations expected to show the highest clinical benefit, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Other features and advantages of the invention will be apparent from the following detailed description and claims.

DETAILED DESCRIPTION OF THE INVENTION

3.1 Definitions

For convenience, the meaning of certain terms and phrases employed in the specification, examples, and appended claims are provided below.

The term "allele" refers to alternative forms of a gene at a particular marker. When a subject has two identical alleles, the subject is said to be homozygous. When a subject has two different alleles, the subject is said to be heterozygous.

"Genotyping" refers to the analysis of an individual's genomic DNA (or a nucleic acid corresponding thereto) to identify a particular disease causing or contributing mutation or polymorphism, directly or based on detection of a mutation or polymorphism (a marker) that is in linkage disequilibrium with the disease causing or contributing gene.

The term "haplotype" refers to a set of alleles that are inherited together as a group (are in linkage disequilibrium). As used herein, haplotype is defined to include those haplotypes that occur at statistically significant levels ($p_{corr} \leq 0.05$). As used herein, the phrase "an IL-1 haplotype" refers to a haplotype in the IL-1 loci including IL-1A, IL-1B and IL-1RN alleles and markers in disequilibrium therewith. "Proinflammatory IL-1 haplotype" refers to a haplotype that is associated with an excess of proinflammatory release (e.g upregulation of functional IL-1α or IL-1β and/or downregulation of a functional IL-1 receptor antagonist.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage equilibrium".

Examples of linked polymorphic markers in linkage disequilibrium with IL-1B(-511) include: the 222/223 marker of IL-1A, the gz5/gz6 marker of IL-1A, the -889 marker of IL-1A, the +6912 marker of IL-1B, the +3953 marker of IL-1B, the gaat.p33330 marker of the IL-1B/IL-1RN intergenic region, the Y31 marker of the IL-lB/ IL-IRN intergenic region, the +2018 allele of the IL-1RN, or the VNTR marker of IL-1RN. Specific alleles of these polymorphic markers are in linkage disequilibrium with allele 1 or allele 2 of IL-1B(-511). For example, linkage disequilibrium analysis between pair-wise combinations of these alleles has established that allele 2 of IL-1B(-511) is in linkage disequilibrium with: allele 4 of IL-1A 222/223, allele 4 of IL-1A gz5gz6, allele 1 of IL-1A -889, allele 1 of IL-1A +3953, allele 3 of the gaat.p3330 marker, allele 3 of the Y31 marker, allele 2 of IL-1B +2018, and allele 2 of the IL-1RN VNTR. Examples of other linked polymorphisms include four polymorphisms in the IL-1RN gene (Clay et al. (1996) Hum. Genet. 97: 723–26). Linkage disequilibrium analysis of these polymorphisms indicates that allele 2 of each is in linkage disequilibrium with allele 2 of IL-1B(-511).

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

"Sepsis", "septicemia", "septic syndrome" and "septic response" refers to those biochemical and physiological responses that have been identified as systemic manifestations of uncontrolled infection. Sepsis is a nonspecific response of the host to any of a variety of factors, including: 1) disseminated microorganisms or their biochemical products from a nidus of infection, 2) microorganisms or their biochemical products without an infected primary source and 3) local inflammatory mediators from an infectious source or from a sterile site without the participation of microorganisms or their biochemical products. Organisms commonly involved in provoking sepsis include Gram positive bacteria, Gram negative bacteria and fungi. As examples, strep and staph species can produce sepsis either from a local focus of infection (a pneumonia or a meningitis, for example) or from a systemic insult (as in toxic shock syndrome). As a further example, sepsis is a well-known concomitant of a genitourinary infection, so-called urosepsis, where the infecting agent is usually a Gram negative organism. *Neisseria meningiditis* may occasion a fulminant, rapidly progressive sepsis accompanying a meningitis. Gram negative organisms commonly produce endotoxin, understood to be bacterial wall lipopolysaccharides that can mediate the responses of sepsis. When endotoxin is involved in sepsis, a key event in the evolution of the syndrome is the activation of the mononuclear phagocyte system, with consequent release of IL-1 and TNF-alpha. Sepsis responses are also understood to follow non-infectious events such as acute pancreatitis. Similar biological events are understood to be able to lead to the septic response following an infectious or a non-infectious insult.

The physiological and biochemical responses characterizing sepsis include: 1) hyperdynamic cardiac parameters, 2) a reduced peripheral vascular resistance, 3) a narrowed arteriovenous oxygen difference and 4) elevated serum lactate levels. There is thought to be a continuum of sepsis that, if uncorrected, may lead to death. The stages of sepsis are understood to be similar to the stages for other types of shock. Shock may result from any serious assault on the body's homeostatic mechanisms, whether from hemorrhage, trauma, burn injury, myocardial infarction or sepsis. Shock consists of widespread hypoperfusion at the tissue level, due to reduction of blood volume, reduction of cardiac output or redistribution of effective circulation. This results in insufficient delivery of oxygen and metabolites to the cells and inadequate clearance of metabolic byproducts. The resultant shift from aerobic to anaerobic cellular metabolism leads to the accumulation of lactic acid in the tissues. The derangements accompanying shock are usually correctable at the outset, but progress to irreversible injury and cellular death.

Stages of sepsis similarly have early reversible changes and later irreversible changes. A staging system has been established to evaluate the extent of the patient's septic deterioration. During the initial, nonprogressive phase, Siegel's Stage A, compensatory mechanisms are activated and vital organ perfusion is maintained. With prolonged insult, this set of responses becomes exaggerated, with clinical symptoms of peripheral vasodilatation combined with decreased perfusion to vital organs. This is Siegel's Stage B. Hypotension may be a consequence of this decreased perfusion. Diminished organ perfusion leads to irreversible injury to vital systems, including the liver, kidney and respiratory failures characteristic of multiple organ failure. The lung has a particular vulnerability to the changes seen in sepsis. A pattern of respiratory failure known as acute respiratory distress syndrome (ARDS) may accompany sepsis as well as other types of shock. As sepsis progresses, there is an increasing cycle of metabolic and circulatory abnormalities until frank shock sets in, as defined herein. Septic shock corresponds to Siegel's Stage C. Progression of shock combined with progression of sepsis leads to the preterminal condition of sepsis-related low output failure, Siegel's Stage D. A patient who has entered this state is considered to have sustained irreversible injury. Survival is not anticipated.

"Neonate sepsis" refers to the set of septic responses, as defined herein, manifest in the newborn infant or the fetus. Neonatal infections may be characterized according to their timing: early neonatal infections tend to occur within several days of birth, while late onset neonatal sepsis becomes manifest after a latent period. Infections with Group B strep or with *Escherichia coil* tend to develop symptoms including sepsis, pneumonia and/or meningitis within four or five days of birth. Infections with Listeria or Candida, by contrast, are later in onset. Infections in infants are termed neonatal infections through the first few months of life. Later infections in infants under age two may also give rise to sepsis. The evaluation of a high fever in this population typically requires vigorous diagnostic interventions to identify a source. A fever of unknown origin (where no source can be found) may be treated aggressively with antibiotics until the possibility of bacteremia can be conclusively ruled out with blood cultures.

3.2 Predictive Medicine 3.2.1. Prognostic Assays and Kits

Based on the findings described in detail in the following examples, that patients homozygous for allele 2 of IL-1B (−511) are more likely to die, the present invention provides methods and kits for determining whether a subject has or is likely to develop sepsis and/or the likely rate or extent of progression of the septicemia.

In one embodiment, the method comprises genotyping a nucleic acid sample obtained from the subject to determine at least one allele of an IL-1 proinflammatory haplotype. For example, an allele of an IL-1 proinflammatory haplotype can be detected, for example, by determining the transcription rate or mRNA and/or protein level of an IL-1 gene or protein, such as by Northern blot analysis, reverse transcription-polymerase chain reaction (RT-PCR), in situ hybridization, immunoprecipitation, Western blot hybridization, or immunohistochemistry. According to one method, cells are obtained from a subject and the IL-1 protein or MRNA level is determined and compared to the level of IL-1 protein or mRNA level in a healthy subject.

In another embodiment, the method comprises measuring at least one activity of an IL-1. For example, the constant of affinity of an IL-1 α or β protein of a subject with a receptor can be determined. The results obtained can then be compared with results from the same analysis performed on a subject, who is known to be either susceptible or not susceptible to sepsis.

In preferred embodiments, the method is characterized as comprising genotyping a nucleic acid sample obtained from the subject to determine at least one allele of an IL-1 proinflammatory haplotype. In an exemplary embodiment, there is provided a nucleic acid composition comprising a nucleic acid probe including a region of nucleotide sequence which is capable of hybridizing to a sense or antisense sequence of at least one allele of an IL-1 proinflammatory haplotype. For example, the nucleic acid can be rendered accessible for hybridization, the probe contacted with the nucleic acid of the sample, and the hybridization of the probe to the sample nucleic acid detected. Such technique can be used to detect alterations or allelic variants at either the genomic or mRNA level as well as to determine MRNA transcript levels.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in sepsis are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, MRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert (*Proc. Natl Acad Sci USA* (1977) 74:560) or Sanger (Sanger et al (1977) *Proc. Nat. Acad Sci* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on IL-1β allele 1 (+6912) is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify IL-1β allele 2 (−511). For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) Mutat Res285:125–144; and Hayashi (1992) Genet Anal Tech Appl 9:73–79). Single-stranded DNA fragments of sample and control IL-1β alleles (−511) are denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *Proc. Natl Acad Sci USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect alleles of an IL-1 proinflammatory haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24:3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No.4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer. J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express the IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Another embodiment of the invention is directed to kits for detecting a predisposition for developing sepsis and/or for progressing more rapidly or severely. This kit may contain one or more oligonucleotides, including 5' and 3' oligonucleotides that hybridize 5' and 3' to at least one allele of an IL-1 proinflammatory haplotype. PCR amplification oligonucleotides should hybridize between 25 and 2500 base pairs apart, preferably between about 100 and about 500 bases apart, in order to produce a PCR product of convenient size for subsequent analysis.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moities, metal binding moities, antigen or antibody moities, and the like.

The kit may, optionally, also include DNA sampling means such as the AmpliCard™ (University of Sheffield, Sheffield, England S10 2JF; Tarlow, J W, et al., J. of Invest. Dermatol. 103:387–389 (1994)) and the like; DNA purification reagents such as Nucleon™ kits, lysis buffers, proteinase solutions and the like; PCR reagents, such as 10X reaction buffers, thermostable polymerase, dNTPs, and the like; and allele detection means such as the HinfI restriction enzyme, allele specific oligonucleotides, degenerate oligonucleotide primers for nested PCR from dried blood.

3.2.2. Pharmacogenomics

Knowledge of the particular IL-1 polymorphisms that are predictive of sepsis, alone or in conjunction with information on other genetic defects contributing to sepsis (the genetic profile of sepsis) allows a customization of the therapy for a particular disease to the individual's genetic profile, the goal of "pharmacogenomics". For example, subjects homozygous for the IL-1B allele 2 (−511) may be predisposed to developing sepsis or for progressing more rapidly or severely into sepsis related sequelae. Thus, comparison of an individual's IL-1 proinflammatory profile to the population profile for sepsis, permits the selection or design of drugs that are expected to be safe and efficacious for a particular patient or patient population (i.e., a group of patients having the same genetic alteration).

The ability to target populations expected to show the highest clinical benefit, based on the IL-1B or disease genetic profile, can enable: 1) the repositioning of marketed sepsis drugs with disappointing market results; 2) the rescue of sepsis drug candidates whose clinical development has been discontinued as a result of safety or efficacy limitations, which are patient subgroup-specific; and 3) an accelerated and less costly development for sepsis drug candidates and more optimal drug labeling (e.g. since the use markers, such as IL-1B allele 2 (−511) is useful for optimizing effective dose).

Cells of a subject may also be obtained before and after administration of a therapeutic to detect the level of expression of genes other than IL-1, to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984);

EXAMPLE 1

A polymorphism of the Interleukin-1 Gene and Death in Meningococcal Disease

A case control study was performed on Caucasian patients aged 4–70 years with documented meningococcal disease, of whom 31 died and 97 survived. DNA from these patients was genotyped for known polymorphisms in the IL-1A gene (at position −889), in the IL-1B gene (at positions −511 and +3954), and the IL-1RN gene intron 2 (+2016) and the TNF α gene (at position −308).

As shown in the following table 1, patients who were homozygous for the rare allele of IL-1B (−511) were more likely to die (odds ratio 5.10; 95% CI 1.61–16.17, P=0.001). Carriage of a single copy of the −511 allele was not significantly associated with death. Polymorphisms with any of the other genes studied were not significantly associated with death.

TABLE 1

Homozygote and Heterozygote frequencies of IL-1 and TNF polymorphisms

| | IL-1A (+4945) | | IL-1B (+3954) | | IL-1B (−511) | | IL-IRA (+2018) | | TNF (−308) | |
|---|---|---|---|---|---|---|---|---|---|---|
| | Homozygote | Heterozygote | Homozygote | Heterozygote | Homozygote | Heterozygote | Homozygote | Heterozygote | Homozygote | Heterozygote |
| Fatal cases (n = 31) | 1 (3.2%) | 14 (45.2%) | 0 (0%) | 12 (38.7%) | 8 (25.8%) | 6 (19.4%) | 5 (16.1%) | 13 (41.9%) | 0 (0%) | 11 (35.5%) |
| Surviving cases (n = 97) | 12 (12.4%) | 40 (41.2%) | 5 (5.2%) | 37 (38.1%) | 6 (6.2%) | 42 (43.2%) | 9 (9.3%) | 37 (38.1%) | 3 (3%) | 25 (25.8%) |

EXAMPLE 2
Identification of IL-1B (−511)

This C/T single base variation in the IL-1 beta promoter was described in di Giovine, F. S. et al., (1992) Hum. Mol. Genet. 1:450. The gene accession number is X04500.

$MgCl_2$ is used at 2.5 mM final and PCR primer (5'-TGGCATTGATCTGGTTCATC-3' (SEQ ID NO: 1) and 5'-GTTTAGGAATCTTCCCACTT-3'(SEQ ID NO: 2) at 1 $\mu$M. Cycling is performed at [95°, 1 min] $\mu$l; [95°, 1 min; 53°, 1 min; 72°, 1 min;] x35; [72, 5 min] $\mu$l; 420 C. Each PCR reaction is divided in two 25 $\mu$l aliquots; one is added of 3 Units of Ava I, the other 3.7 Units of Bsu 36 1, in addition to 3 $\mu$l of the specific 10X restriction buffer. Incubation is at 37° C. overnight. Electrophoresis is by PAGE 9%.

Interpretation

The two enzymes cut respectively the two different alleles. Ava I will produce 190+144 for allele 1, while it does not cut allele 2 (304 bp). The restriction pattern obtained should be the inverse in the two aliquots (identifying homozygotes) or identical (heterozygotes). Frequencies in North British Caucasian population are 0.61 and 0.39. For 90% power at 0.05 level of significance in a similar genetic pool, 133 cases should be studied to detect 1.5 fold increase in frequency, or 505 for 0.1 absolute increase in frequency.

What is claimed is:

1. A method for predicting the severity with which an infected subject is likely to develop sepsis, said method comprising the steps of:

a) obtaining a nucleic acid sample from the subject; and b) detecting at least one allele in linkage disequilibrium with IL-1B (−511) allele 2 in said sample;

wherein said at least one allele is located in the promoter of the IL-1B gene and wherein detection that the sample is homozygous for said at least one allele indicates that the subject is likely to develop severe sepsis.

2. A method of claim 1 wherein the subject has been infected with *Neisseria meningiditis*.

3. A method of claim 1 wherein said step of detecting at least one allele comprises nucleic acid amplification.

4. A method of claim 3 wherein said nucleic acid amplification comprises polymerase chain reaction (PCR).

5. A method of claim 3 wherein said step of detecting comprises digestion with a restriction enzyme.

6. A method of claim 5 wherein said restriction enzyme is Bsu36I or AvaI.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 1
tggcattgat ctggttcatc                                           20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 2
gtttaggaat ctcccactt                                            20

7. A method for predicting the severity with which an infected subject is likely to develop sepsis, said method comprising the steps of:
   a) obtaining a nucleic acid sample from the subject; and
   b) detecting IL-1B (−511) allele 2 in said sample; wherein detection that the sample is homozygous for said allele indicates that the subject is likely to develop severe sepsis.

* * * * *